United States Patent [19]

Johansson et al.

[11] Patent Number: 5,195,890
[45] Date of Patent: Mar. 23, 1993

[54] DEVICE AND METHOD FOR SUPPORTING ARTIFICIAL TEETH

[75] Inventors: Stig Johansson; Anders Lindberg, both of Åhus, Sweden

[73] Assignee: Titanbron I Åhus AB, Stormgatan, Sweden

[21] Appl. No.: 689,775
[22] PCT Filed: Nov. 24, 1989
[86] PCT No.: PCT/SE89/00688
§ 371 Date: May 15, 1991
§ 102(e) Date: May 15, 1991
[87] PCT Pub. No.: WO90/05499
PCT Pub. Date: May 31, 1990

[30] Foreign Application Priority Data
Nov. 24, 1988 [SE] Sweden ................ 8804257

[51] Int. Cl.$^5$ ............... A61C 13/12; A61C 13/225; A61C 8/00; A61C 11/00
[52] U.S. Cl. ................. 433/172; 433/173; 433/213; 433/215
[58] Field of Search ............ 433/167, 171, 172, 173, 433/174, 199.1, 200.1, 213, 215

[56] References Cited

U.S. PATENT DOCUMENTS

| | | | |
|---|---|---|---|
| 4,516,937 | 5/1985 | Bosker | 433/173 |
| 4,645,453 | 2/1987 | Niznick | 433/173 |
| 4,758,161 | 7/1988 | Niznick | 433/173 |
| 4,784,608 | 11/1988 | Mays | 43/172 |
| 4,850,870 | 7/1989 | Lazzara et al. | 433/174 |
| 4,906,189 | 3/1990 | Knapp | 433/173 |
| 4,906,191 | 3/1990 | Söderberg | 433/213 |
| 4,931,016 | 6/1990 | Sillard | 433/172 |
| 4,968,250 | 11/1990 | Small | 433/173 |
| 5,007,833 | 4/1991 | Barbone | 433/173 |

FOREIGN PATENT DOCUMENTS

| | | |
|---|---|---|
| WO88/03007 | 5/1988 | PCT Int'l Appl. . |
| 448599 | 3/1987 | Sweden . |
| 455156 | 6/1988 | Sweden . |
| 455369 | 7/1988 | Sweden . |
| 458499 | 4/1989 | Sweden . |
| 458500 | 4/1989 | Sweden . |
| 2119258 | 2/1985 | United Kingdom . |

OTHER PUBLICATIONS

Niznick, Implant Prosthodontics Using the Core-Vent System, Jour, Oral Implant. vol XII, No. 1, 1985.
Jemt, Modified Single and Short-Span . . . , Jour. Prosth. Deng., Feb. 1986, vol. 55, No. 2 Tissue-Integrated Prostheses, Quintessence, Publishing Co., Inc., 1985.

Primary Examiner—John J. Wilson
Assistant Examiner—Cindy A. Cherichetti
Attorney, Agent, or Firm—Kane, Dalsimer, Sullivan, Kurucz, Levy, Eisele and Richard

[57] ABSTRACT

A device for supporting artificial teeth, which device is intended to be secured to anchoring elements in a jaw, includes tubes, which are secured to the anchoring elements, and a bridge formed as an integral piece and fixed to the end surfaces of the tubes. The end surface of each tube is in the same plane as the corresponding engagement surface on the bridge. For making the device, one or more planes are determined, giving the bridge a suitable position in relation to the anchoring elements, and the tubes are cut such that their end surfaces will be located in the planes when the device has been secured to the anchoring elements. Each of the engagement surfaces of the bridge is thereafter processed so as to be located in the same plane as the end surface of the corresponding tube, and the bridge is finally secured to the tubes by welding.

12 Claims, 2 Drawing Sheets

DEVICE AND METHOD FOR SUPPORTING ARTIFICIAL TEETH

The present invention relates to a device for supporting artificial teeth, which is intended to be secured to anchoring elements embedded entirely or partially in a jaw.

The invention also relates to a method for making the device.

It happens quite often, as a consequence of a disease or an accident, that people lose several teeth in one or both jaws. These teeth must be replaced by artificial ones, which may be done, for instance with the aid of a detachable denture, fixed bridges or, as in the case of the present invention, a denture permanently anchored in the jaw bone.

Different methods and devices are currently used for anchoring a denture in the jaw bone. A method and a device generally used in Swedish dentistry will be described hereinbelow.

The first step to be taken, after examination and thorough diagnosis, is to insert anchoring bodies, sometimes referred to as fixtures, in the jaw bone by surgical operation, in the area of the jaw where the denture is to be fixed. The anchoring body may consist e.g of a screw of titanium, having an external and an internal thread.

When the anchoring bodies after healing are fixed in the jaw, the surgeon loosens the flap of the mucous membrane covering the anchoring bodies during the healing process so as to expose the anchoring bodies. In each anchoring body is then fixed a spacer member of titanium by means of a screw which is screwed in the internal thread of the anchoring body. The spacer member extends through the mucous membrane in the jaw and is axially aligned with the anchoring body. One spacer member and one anchoring body together form an anchoring element to which a denture can be permanently secured.

In a jaw without any teeth, parts of the bone will gradually be resorbed. Thus, the number of sites where anchoring bodies can be implanted will be limited This, together with the fact that there is no easy way for controlling the orientation and the depth of the anchoring bodies when implanting them in the jaw bone, entails that the anchoring bodies, and thus the spacer members, may be inclined in relation to each other and that the spacer members may protrude over the mucous membrane to a varying degree.

After the spacer members have been mounted on the anchoring bodies, a model is prepared of the jaw, as it appears with the implanted anchoring bodies and the spacer members fixed thereto. To this end, impression elements are screwed to the spacer members, and an impression is made of the jaw in this state. When the impression has set, the impression elements are removed from the spacer members, whereupon the entire plaster impression can be removed from the jaw. Model spacer members and model anchoring bodies of brass are then screwed into the impression elements so as to have the same inclination and vertical position as the real anchoring bodies and spacer members in the jaw, and the impression is filled with plaster. When the plaster has hardened and the impression with the impression elements has finally been loosened from the plaster with the brass anchoring bodies and brass spacer members, an exact model of the jaw has been obtained.

In this connection, a plaster model of the other jaw is also prepared Finally, the patient will have to bite in a soft mass, thus providing a bite impression showing how the patient's jaws are located in relation to each other and thus what space is available for building up an artificial row of teeth.

The plaster models of the patient's jaws are fixed in an artificial jaw-joint which, on the basis of the bite impression, is adjusted so as to agree with the patient's bite.

To the model of the toothless jaw is then applied a wax ridge in which artificial teeth are placed in a manner to provide a correct bite and an aesthetic appearance. As a final check, the wax ridge with the teeth inserted therein is tried in the patient's mouth.

The wax ridge serves as a model for the bridge which is to be cast in the next step and which eventually should support the artificial teeth. It is therefore moulded after the jaw and provided with holes registering with the spacer members to make it possible to subsequently screw the finished bridge to the spacer members.

When the wax model is finished, it is enclosed in a mold, whereupon the wax is evaportated and gold is slung into the mold.

When the gold solidifies, it however undergoes dimensional changes, which sometimes means that the gold bridge thus cast will not fit exactly on the spacer members, which in turn means that the spacer members and anchoring bodies would be subjected to undesired stresses if the bridge were mounted in this state. Thus, the gold bridge must be modified, which is done by sawing it off at one or more points, adjusted to the spacer members and finally soldered together.

When the gold bridge is finished, it is provided with gingive-like plastic and artificial teeth, holes being left in the extension of the holes in the bridge. The denture is thereafter ready for mounting in the patient's mouth by means of screws which are passed through the holes in the plastic and the bridge and screwed in the internal thread in the head of the screw holding the spacer member and the anchoring body together. Finally, the holes in the plastic are filled with plastic and ground smooth.

As mentioned above, this method of preparing, trying out and fixing a denture in the patient's jaw is generally used in Sweden today This technique however entails different problems.

A first problem is that it demands considerable efforts and is time-consuming.

A second problem is that the gold in the bridge and the titanium in the spacer members may together give rise to undesired electrochemical reactions in the mouth.

A third problem is linked with the above-mentioned resorption in the jaw. If there have not been any teeth in the jaw for a long time, it may be heavily resorbed. This in turn means that the distance between the toothless jaw and the opposite jaw is considerable and that a substantial build-up of the toothless jaw is required for placing the aritificial teeth on a correct height for a proper bite. In other words, the gold bridge must have sufficient strength and a considerable extent in the vertical direction, which makes it heavy. This may cause discomfort to the patient.

A fourth problem which is related to the material used in the bridge and the weight thereof is the cost aspect. Since gold is an expensive material and there is required as much as between 15 and 40 g for a regular bridge, it will be expensive to make.

A fifth problem is the above-mentioned dimensional change in connection with casting, making it difficult to produce a bridge which, when secured to the anchoring bodies and the spacer members, does not give rise to stresses between the different anchoring bodies.

A sixth problem is that, when trying out the spacer members, the mucous membrane is often swollen because of the surgical operation for exposing the anchoring bodies and the aesthetic administered in this connection, which may result in that too long spacer members are mounted in the anchoring bodies. When the swelling in the mucous membrane disappears, the spacer members will project to an excessive extent above the mucous membrane, which is less desirable from the aesthetic point of view.

The above-mentioned problems are well known to those skilled in the art, and many attempts have been made to solve them.

One proposal for a solution is described in Swedish patent application 8605272-7. This document describes a bridge which, as in the case related above, is anchored in the jaw by means of anchoring bodies and spacer members. In this case, the bridge is made up of a number of bridge elements, each of which consists of a mounting member screwed in a spacer member, and two wings projecting on each side of the mounting member towards the wing on the bridge element of the adjacent spacer member. When building up the bridge, the bridge elements are fitted to each other, and connecting surfaces are prepared between the bridge elements. When all bridge elements have been adjusted to each other, the bridge is welded together at the connecting surfaces and provided with plastic and teeth in customary manner.

The bridge of this design is made of titanium, which eliminates the problems of undesired electrochemical reactions and also reduces the weight and the price of the bridge.

The bridge described in SE 8605272-7 however suffers from other drawbacks as well. Since the spacer members, as described above, are inclined and located on different vertical levels in relation to each other, it is a complicated matter to adjust the bridge elements to each other in a manner to obtain accurate connecting surfaces. Further, if the jaw is slightly resorbed, it is difficult to achieve a suitable bite level since the bridge elements are not vertically adjustable in the same manner as the known gold bridge mentioned above, but may require too much space. If the jaw is heavily resorbed, it may be necessary to place the row of teeth at a considerable distance in the sagittal direction in front of the bridge proper. In such a case, there may be a problem of insufficient strength since the teeth are not supported by the bridge.

The object of the present invention thus is to provide a device for supporting artificial teeth in a jaw and a method for making the device, in order to solve the above-mentioned problems inherent in the prior art technique.

This object is achieved by means of a device and a method having the features stated in the claims.

According to the invention, extension members and a tooth-supporting means are cut such that the end surface of each extension member is located in the same plane as the corresponding engagement surface of the tooth-supporting means in the finished device. By means of the extension members the height above the anchoring elements of a bridge and, hence, of the artificial teeth fixed thereon can easily be adjusted according to the patient's needs, so as to provide a suitable bite level, whether the bone in the jaw is slightly or heavily resorbed. The end surfaces of the extension members also form a seat on which the tooth-supporting means, which may consist of a prefabricated beam obtained by casting, milling or sawing, can easily be secured. Since the extent of the bridge in the sagittal direction can be adjusted according to the patient's needs, the row of artificial teeth will also be constantly supported by the bridge from the side of the anchoring bodies, thus providing sufficient strength. Since the device consists of a tooth-supporting means and extension members which are welded in an accurately defined position to the tooth-supporting means, the device can be secured to the anchoring bodies or the spacer members without any stresses arising therebetween. By means of the extension members it is also possible to solve the problem of excessively long spacer members, whereby to provide an aesthetically pleasing denture.

Embodiments of the present invention will be described hereinafter with reference to the accompanying drawings, in which FIG. 1 schematically shows a plurality of anchoring bodies implanted in the jaw, and spacer members secured to the anchoring bodies, one anchoring body and one spacer member being shown in cross-section;

Figure 1:
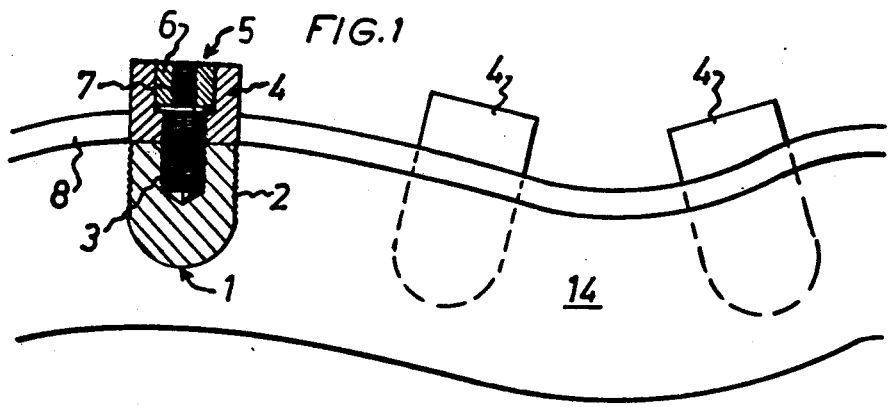

FIG. 1 shows anchoring bodies and spacer members in a jaw. Anchoring bodies 1 with an external thread 2 and an internal thread 3 are implanted in the dentine 14. A spacer member 4 is fixed in each anchoring body 1 by a screw 5 screwed in the internal thread 3 of the anchoring body and having a head 6 with an internal thread 7. The spacer members 4 extend through the mucous membrane 8 in the jaw and project slightly over it. In this context, it should be pointed out that the spacer members should project as little as possible above the gums. In the Figures, the height of the spacer members over the gums thus is exaggerated. As earlier mentioned and as also appears from the Figure, the spacer members are slightly inclined in relation to each other and are also on different vertical levels over the mucous membrane 8.

When the spacer members have been secured to the anchoring bodies, a model of each jaw is made and a bite impression is taken, as described above.

Figure 2:
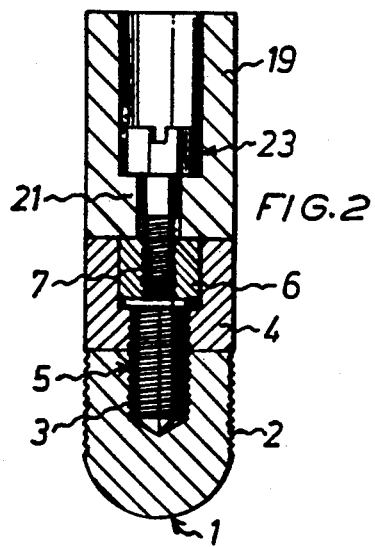
FIG. 2 is a cross-section schematically showing a tube according to the invention when mounted on a spacer member, in turn mounted on an anchoring body.

As shown in FIG. 2, a tube 19 is thereafter fixed in each spacer member 4 on the model of the toothless jaw. This tube is cylindrical and has an end shaped to fit on the spacer member 4. The tube 19, preferably turned and made of titanium, further has an internal, annular abutment 21 at its end facing the spacer member. The tube 19 is secured to the spacer member 4 by a screw 23 which is passed through the tube and screwed in the internal thread in the head 6 of the screw 5, such that the screw 23 enters into engagement with the abutment 21 in the tube. The longitudinal axis of the tube 19 will thus be aligned with the longitudinal axis of the spacer member 4 and the anchoring body 1.

The model with the tubes 19 screwed to it is thereafter fixed in the artificial jaw-joint, and a plane through the tubes giving the patient a correct bite level is determined and marked.

Figure 3:
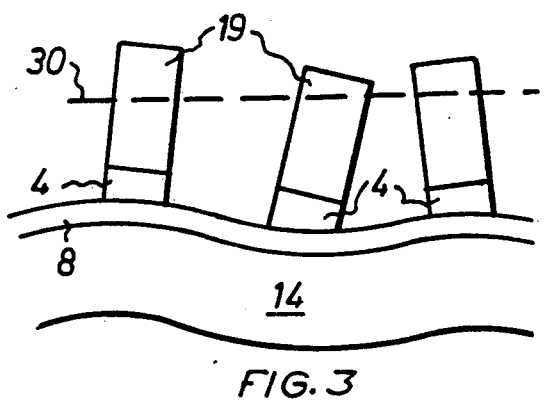
FIG. 3 is a schematic side view showing a jaw with spacer members and tubes mounted therein.

FIG. 3 shows the model of the jaw with spacer members 4 and tubes 19 mounted thereon. It appears from this Figure that the spacer members 4 are slightly inclined in relation to each other and also are located on different vertical levels, which in turn means that the tubes will be inclined in relation to each other and that their free end surfaces will be on different vertical levels. The plane 30 in which the tubes 19 should be cut is indicated by a dashed line in the Figure.

The model with the tubes is then moved to a spark erosion machine of the wire electrode type, in which the tubes are cut to the indicated height, such that the free end surface of each tube will be located in the indicated plane 30.

In the artificial jaw-joint, the suitable shape of a bridge to support the artificial teeth is then determined as well as a suitable position therefor in the sagittal direction. This can be done, for instance by using a mouldable material and making a model of the bridge on the model jaw in the artificial jaw-joint.

When this model is finished, the bridge is cut e.g. from a titanium sheet. The bridge can also be made from a prefabricated beam obtained by casting, milling or sawing. According to a further variant, the bridge can be cast by the model.

In the same manner as in the case of the tubes 19, the bridge is cut in a plane by wire electrode spark erosion, such that the surfaces of the bridge engaging the end surfaces of the tubes will be in a common plane. The areas of the bridge between the engagement surfaces can thereafter be shaped as desired.

Figure 4:
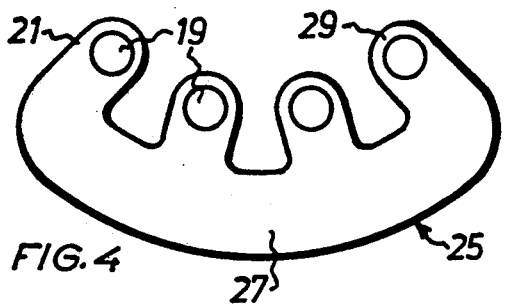
FIG. 4 is a top plan view schematically showing one example of a bridge mounted on tubes.

FIG. 4 schematically shows a possible appearance from above of a bridge 25 when mounted on the tubes 19. The bridge has been cut from a metal sheet and has an arcuate portion 27 which conforms to the shape of the jaw and above which the artificial teeth should be placed. From the arcuate portion, tongues 29 extend which are fixed to the tubes 19.

Figure 5:
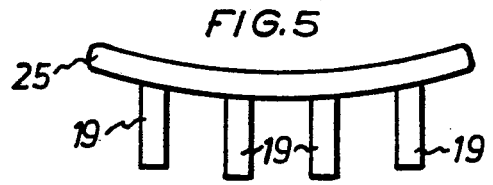
FIG. 5 is a side view showing another example of a bridge mounted on tubes.

FIG. 5 shows another example of a bridge 25. In this case, the bridge consists of a narrow beam provided straight above the tubes 19.

When the beam has been correctly positioned on the tubes, it is fixed thereto, for instance by laser welding. The plaster in the model is thereafter removed, such that the model anchoring bodies and the model spacer members can be exposed and unscrewed from the tubes. The beam and the tubes are placed in a jig, and holes are made through the beam in the extensions of the tubes. The holes may be provided e.g. by drilling. The beam is thereafter provided in known manner with plastic or porcelain or composite material, as well as artificial teeth, and is to the patient's jaw, whereupon the screw holes in the plastic are filled.

Another currently preferred embodiment of the invention will now be described with reference to FIGS. 6-8.

In the same manner as in the prior art, anchoring bodies are inserted by surgical operation in the patient's jaw, and a model 60 of the jaw with anchoring bodies and spacer members 4 mounted therein is prepared.

Figure 6:
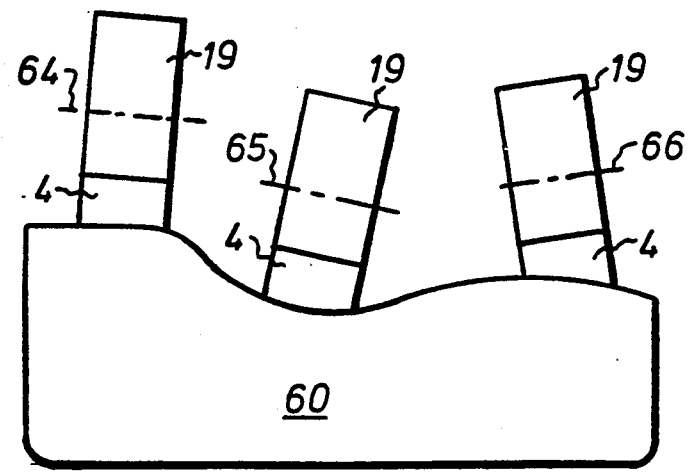
FIG. 6 is a schematic side view showing a model with tubes mounted thereon according to another embodiment of the invention.
Figure 7:
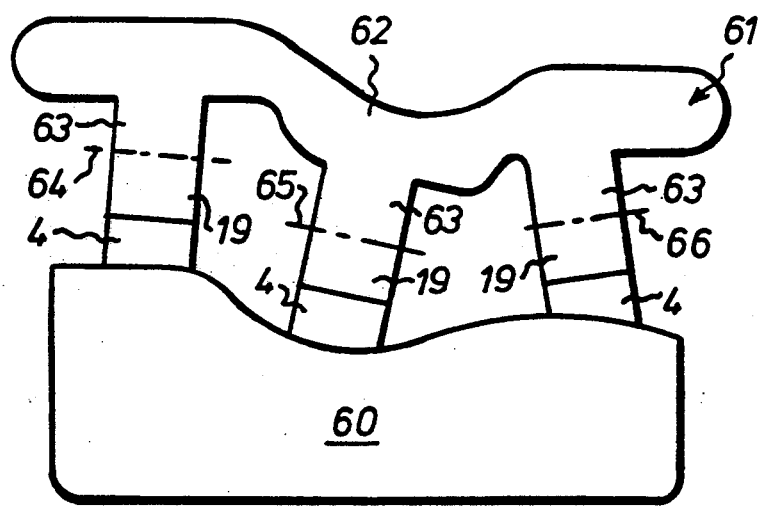
FIG. 7 is a schematic side view showing the same model as in FIG. 6 with a cast beam mounted thereon.

Tubes 19 are thereafter fixed in the spacer members 4 in the model 60, as shown in FIG. 6, and a plane 64-66 is determined for each tube, giving a suitable length to the tube and, thus, a suitable position for a tooth-supporting bridge with respect to the location of the anchoring bodies. The planes are then elected so as to be located as close to the spacer members as possible. The planes 64-66 may, but need not necessarily be mutually parallel or be located in one and the same plane. If the planes are not parallel, they should preferably be at right angles to the longitudinal axes of the anchoring bodies.

When the planes have been determined, the model 60 with the tubes 19 is fixed in a suitable cutting machine, and the tubes 19 are cut in said planes 64-66. Cutting can be effected, e.g. by wire electrode spark erosion, laser cutting or sawing.

On the cut tubes 19 on the model 60 is thereafter made a wax model of a bridge 61 having a laterally extending portion 62 and legs 63 (see FIG. 7) projecting therefrom. On the basis of this wax model, a bridge 61 of titanium is cast. The surfaces of the bridge intended to engage the tubes 19 are then processed so as to fit exactly on the tubes 19 in the planes 64-66. Such processing may consist in removing burrs and other casting defects or of a cutting operation similar to that performed on the tubes.

Finally, the cast bridge 61 with the legs 63 is welded onto the cut tubes 19, such that the bridge 61 and the tubes 19 form a device which fits exactly on the spacer members in the patient's jaw and which can thus be fixed thereon without any stresses arising between the anchoring bodies.

If, on the other hand, a bridge had been moulded and cast directly on the spacer members, stresses would most probably have occurred between the anchoring bodies when mounting the bridge in the patient's jaw because of dimensional changes in connection with casting. These dimensional changes are now instead taken up in the joints 64-66 between the tubes and the bridge. In this context, it should be pointed out that it is important that the end surface of each tube and the corresponding engagement surface of the bridge are located in a common plane, so that no stresses arise when mounting the bridge on the tubes.

The method and devices described above can be modified in many different ways within the scope of the accompanying claims. For instance, it is possible to secure the tubes directly to the anchoring bodies, in which case the spacer members can be dispensed with. The material used for the bridge and the tubes preferably is titanium, but also other materials are conceivable. The tubes can be shortened in many different ways. For instance, the wire electrode spark erosion technique stated above may be replaced by surface grinding or laser cutting. Further, the bridge can be fixed to the tubes in many different ways, for instance by gluing, screwing or soldering. The device according to the invention may of course also be fixed to anchoring bodies and spacer members of a design different from that now described and shown. The shape and the cross-section of the tubes may also be modified.

We claim:

1. Device for supporting artificial teeth, comprising at least two non-bendable extension members and a tooth-supporting means extending therebetween, said extension members and said tooth-supporting means being an integral piece, each said extension member having a first end and a second end, said first end and said second end having end surfaces, said first end being securable to an anchoring element embedded in a jaw, said extension members forming extensions of said anchoring elements and having the same angles between their longitudinal axes as said anchoring elements, said tooth-supporting means extending between said extension members and being fixed to said second ends of said extension members, wherein at least one of said extension members has an end surface of its second end making an angle which is different from zero with the end surface of its first end, wherein said angle between the first and the second end surface is such that the second end surfaces of said extension members are located in and define parallel planes, and wherein said tooth-supporting means is fixed to said extension members prior to said use of the device in the jaw, said tooth-supporting means and said extension members being an integral piece, said tooth-supporting means having surfaces for engaging the extension members, said surfaces being located in said planes of their respective extension members.

2. Device as claimed in claim 1, wherein the tooth-supporting means (25) is a beam formed as an integral piece.

3. Device as claimed in claim 1, wherein tooth-supporting means is a cast structure.

4. Device as claimed in claim 1, wherein the second end surfaces of the extension members are located in one and the same plane.

5. A method for making a device for supporting artificial teeth, said device being securable to anchoring elements embedded entirely or partially in a jaw, said method comprising the steps of:
providing non-bendable extension members securable to said anchoring elements,
providing a tooth-supporting means securable to said extension members at engagement surfaces thereon and extending therebetween,
determining a plane through each of said extension members, said planes being parallel to one another and defining a desired position for said tooth-supporting means relative to said anchoring elements,
shortening the extension members such that their end surfaces facing said tooth-supporting means are located in their respective planes when said extension members are secured to said anchoring elements,
processing said engagement surfaces of said tooth-supporting means which are to engage said extension members to place said engagement surfaces in the same planes as said end surfaces of their respective extension members when the device is secured to the anchoring elements; and
securing the tooth-supporting means to the extension members to form an integral structure.

6. Method as claimed in claim 5, wherein the extension members (19) are shortened by wire electrode spark erosion type cutting.

7. Method as claimed in claim 5, wherein the extension members (19) are shortened by laser cutting.

8. Method as claimed in claim 6, wherein holes which are axially aligned with the longitudinal axis of the respective extension member (19) are provided through the tooth-supporting means (25) when this has been secured to the extension members.

9. Method as claimed in claim 6, wherein the tooth-supporting means (25) is secured to the extension members by welding.

10. Method as claimed in claim 5, wherein said parallel planes through said extension members form a common plane.

11. A method for making a device for supporting aritificial teeth, said device being securable to anchoring elements embedded entirely or partially in a jaw, said method comprising the steps of:
embedding at least two anchoring elements int he jaw of a dental patient;
attaching an impression element into each of said anchoring elements;
making an impression of the jaw of the dental patient;
removing said impression elements form said anchoring elements;
removing said impression form the jaw of the dental patient;
attaching said impression elements to model anchoring elements;
inserting said impression elements, attached to said model anchoring elements, into said impression;
filling said impression with plaster and allowing said plater to harden;
removing said impression and said impression elements from said plaster to obtain an exact model of the jaw of the dental patient with said model anchoring elements embedded therein;
providing non-bendable extension members securable to said anchoring elements;
providing a tooth-supporting means securable to said extension members at engagement surfaces thereon and extending therebetween;
attaching said extension members to said model anchoring elements in said model of the jaw of the dental patient;
determining a plane through each of said extension members, said planes being parallel to one another and defining a desired position for said tooth-supporting means relative to said anchoring elements;
shortening said extension members such that their end surfaces facing said tooth-supporting means are located in their respective planes;
processing said engagement surfaces of said tooth-supporting means which are to engage said extension members to place said engagement surfaces in the same planes as said end surfaces of their respective extension members;
securing said tooth-supporting means to said extension members to form said device for supporting artificial teeth as an integral structure; and
removing said device from said model of the jaw of the dental patient.

12. Method as claimed in claim 11, wherein said parallel planes through said extension members form a common plane.

* * * * *